(12) United States Patent
Saxena et al.

(10) Patent No.: US 8,541,435 B2
(45) Date of Patent: Sep. 24, 2013

(54) NIACIN COMPOSITIONS FOR REDUCTION OF AMYLOID BETA PEPTIDE 42 (ABETA 42) PRODUCTION AND FOR TREATMENT OF ALZHEIMER'S DISEASE (AD)

(76) Inventors: Uday Saxena, Atlanta, GA (US); Venkateswarulu Akella, Hyderabad (IN)

( * ) Notice: Subject to any disclaimer, the term of this patent is extended or adjusted under 35 U.S.C. 154(b) by 245 days.

(21) Appl. No.: 12/737,323

(22) PCT Filed: Jul. 9, 2009

(86) PCT No.: PCT/US2009/004015
§ 371 (c)(1), (2), (4) Date: Dec. 31, 2010

(87) PCT Pub. No.: WO2010/005581
PCT Pub. Date: Jan. 14, 2010

(65) Prior Publication Data
US 2011/0097347 A1    Apr. 28, 2011

Related U.S. Application Data

(60) Provisional application No. 61/134,593, filed on Jul. 11, 2008.

(51) Int. Cl.
*A61K 31/435* (2006.01)
*C07D 213/79* (2006.01)

(52) U.S. Cl.
USPC .................................. 514/277; 546/326

(58) Field of Classification Search
None
See application file for complete search history.

(56) References Cited

U.S. PATENT DOCUMENTS

| | | |
|---|---|---|
| 2003/0158237 A1 | 8/2003 | Saragovi |
| 2004/0185123 A1 | 9/2004 | Mazzio |
| 2005/0147620 A1 | 7/2005 | Bozicevic |
| 2007/0065456 A1 | 3/2007 | Woods |

FOREIGN PATENT DOCUMENTS

| WO | WO 96/32942 | 10/1996 |
|---|---|---|
| WO | WO 99/06035 | 2/1999 |

OTHER PUBLICATIONS

Morris et al., "Dietary niacin and the risk of incident Alzheimer's disease and of cognitive decline", Journal of Neurology Neurosurgery & Psychiatry, vol. 75, No. 8, 2004, pp. 1093-1099.
Leuchetenberger, et al., "Selective Modulation of a Beta 42 Production in Alzheimer's Disease: Non-Steroidal Anti-Inflammatory Drugs and Beyond", Current Pharmaceutical Design, vol. 12, No. 33, 2006, pp. 4337-4355.
International Search Report received for PCT Patent Application No. PCT/US2009/004015, mailed on Oct. 27, 2009, 5 pages.
Thambusamy Pushpanathan et al., "The essential oil of Zingiber officinalis Linn (Zingiberaceae) as a mosquito larvicidal and repellent agent against the filarial vector Culex quinquefasciatus Say (Diptera: Culicidae)", Parasitology Research, vol. 102, No. 6, 2008, pp. 1289-1291.
Anekonda et al., "Can herbs provide a new generation of drugs for treating Alzheimer's disease?", Brain Research Reviews, vol. 50, No. 2, 2005, pp. 361-376.
Hirohata, et al., "Non-steroidal anti-inflammatory drugs have anti-amyloidogenic effects for Alzheimer's beta amyloid fibrils in vitro", Nueropharmacology, vol. 49, No. 7, 2005, pp. 1088-1099.
Hamaguchi, et al., "Anti-amyloidogenic therapies: strategies for prevention and treatment of Alzheimer's disease", CMLS Cellular and Molecular Life Sciences, vol. 63, No. 13, 2006, pp. 1538-1552.
Irie,Yoshifumi, et al., "Rhizoma acori graminei and its active principles protect PC-12 cells from the toxic effect of amyloid-beta peptide", Brain Research, vol. 963, No. 1-2, 2003, pp. 282-289.
Van Leyen, Klaus, et al., "Novel lipoxygenase inhibitors as neuroprotective reagents", Journal of Neuroscience Research, vol. 86, No. 4, 2008, pp. 904-909.
Sadeghian, et al., "Design and synthesis of eugenol derivatives, as potent 15-lipoxygenase inhibitors", Bioorganic & Medicinal Chemistry, vol. 16, No. 2, 2007, pp. 890-901.

*Primary Examiner* — Savitha Rao
*Assistant Examiner* — Gregg Polansky
(74) *Attorney, Agent, or Firm* — Patent GC; Naomi S. Biswas (57) ABSTRACT

The present invention discloses (1) phenolic ester hybrids of niacin with m-methoxy-p-hydroxy phenyl compounds like eugenol, vanillin, apocynin, ferulic acid, isoferulic acid and eugenol epoxide and (2) cocrystals of hybrids as above, particularly cocrystal of niacin-eugenol hybrid with cocrystal former like eugenol and oxalic acid (3) novel pharmaceutical compositions comprising a combination of niacin and one or more small molecule/potentiating agent like eugenol, curcumin, cinnamic acid, meclofenamic acid, and their use in the treatment of a disorder or a disease caused by excess production of amyloid beta peptide-42 (Aβ42), its deposition, accumulation, and plaque formation including Alzheimer's Disease, dementia and mild cognitive impairment as well as other neurodegenerative diseases such as Parkinson's Disease and ischemic stroke.

6 Claims, 4 Drawing Sheets

Figure 3: Concentration Response Curve In presence of eugenol

Figure 4: Concentration Response Curve In presence of meclofenamic acid

Figure 5: Concentration Response Curve In presence of curcumin

Figure 6: Concentration Response Curve In presence of cinnamic acid

NIACIN COMPOSITIONS FOR REDUCTION OF AMYLOID BETA PEPTIDE 42 (ABETA 42) PRODUCTION AND FOR TREATMENT OF ALZHEIMER'S DISEASE (AD)

RELATED APPLICATIONS

This application claims priority from U.S. Provisional Patent Application No. 61/134,593 filed 11 Jul. 2008 and is incorporated herein by reference in its entirety.

FIELD OF THE INVENTION

The present invention relates to (1) phenolic ester hybrids of niacin with m-methoxy-p-hydroxy phenyl compounds like eugenol, vanillin, apocynin, ferulic acid, isoferulic acid and eugenol epoxide and (2) cocrystals of hybrids as above, particularly cocrystal of niacin-eugenol hybrid with cocrystal former like eugenol and oxalic acid (3) novel pharmaceutical compositions comprising a combination of niacin and one or more small molecule/potentiating agents like eugenol, curcumin, cinnamic acid, meclofenamic acid useful for the treatment of a disorder and/or a disease caused by excess production of amyloid beta peptide-42 (Aβ42), its deposition, accumulation, and plaque formation. The compounds and combinations of this invention is used in the treatment of Alzheimer's Disease, dementia and mild cognitive impairment as well as other neurodegenerative diseases such as Parkinson's Disease and ischemic stroke.

BACKGROUND OF THE INVENTION

Alzheimer's disease (AD) is a chronic and progressive neurodegenerative disorder which severely effects cognitive function and other behavioral aspects such as executive function and language skills. AD will become world's largest economic healthcare burden over the coming decades. AD is thought to affect 10% of the population over 65 years of age and much more for those over age 80, with the numbers continuing to increase with longevity. Current U.S. estimates on the number of patients suffering from the disease range from three to five million, with an annual estimated cost of over $100 billion dollars. It is estimated that by 2050 the number of patients with AD could be as high as 25 million. This disease not only presents an economic burden but there cannot be a value attached to the emotional burden for the family and friends of the disease who have to provide care for the patients after cognitive dysfunction sets in. Many of the patients continue to live long lives despite the cognitive dysfunction. Despite this severe unmet need, the current marketed drugs are useful only in treating the symptoms of the disease and do not intervene in disease causing mechanism(s) which could stop or reverse the disease.

The disease was first described in 1907 by Alois Alzheimer and is characterized by a progressive loss of neurons and synapses with the presence of large numbers of extracellular amyloid plaques. The dominant scientific theory for genesis of AD is called "amyloid hypothesis" (See Science, 2002, 297(5580):353-6). According to this beta-amyloid cascade hypothesis, the accumulation of beta-amyloid (Aβ) peptides as amyloid plaques in the patient's brain is the primary triggering event in the pathogenesis of Alzheimer's disease (AD). Amyloid plaques are formed by excess production of amyloid beta peptides (Aβ) primarily by neurons. Both extracellular and intracellular accumulation of Aβ initiates a cascade of events including synaptic and neuritic injury, microglial and astrocytic activation (inflammatory response), altered neuronal ionic homeostasis, oxidative damages, changes of kinases/phosphatases activities, formation of NFTs, and finally cell death. Visible pathological changes such as amyloid plaque formation and neurofibrillary tangles (NFTs) are a consequence of Aβ deposition.

Amyloid beta peptide (Aβ) is generated during the proteolytic processing of the parent beta-amyloid precursor protein (APP). APP is a transmembrane protein with domains spanning the membrane. The membrane spanning domains are hydrophobic and the cleavage of this region generates hydrophobic peptides called Aβ peptides (See Trends Cell Biol. 1998, 8:447-53). The enzymatic cleavage of APP is catalyzed by a set of enzymes called alpha-, beta-, and gamma-secretases (See J Clin Invest. 1999, 104:1321-7). Peptides generated by proteolysis can either be non-amyloidogenic meaning they do not form plaques or they can be amyloidogenic which means they aggregate and form clumps (oligomers of various sizes) and eventually plaques. The alpha-secretase mediated enzymatic cleavage releases non-amyloidogenic peptides considered harmless. The beta-secretase and gamma-secretase working in tandem generate Aβ40 and/or Aβ42. Aβ42 is neurotoxic and more hydrophobic than Aβ40, thus it has stronger tendency to oligomerize and aggregate.

The strongest evidence for a pathogenic role of Aβ peptides in Alzheimer's comes from human mutations in APP and presenilin, the enzyme complex component of gamma-secretase. The majority of known APP and presenilin mutations responsible for familial early onset AD affect APP processing causing overproduction of Aβ peptides, especially Aβ42. Given the acceptance that generation of Aβ42 is fundamental to plaque formation, this has led to attempts to develop therapies based upon blocking the generation of Aβ42. In addition several in vitro and in vivo studies using models of Alzheimer's have also supported a role for production of Aβ peptides being a causative event. Therefore, several strategies are being employed by the pharmaceutical industry to decrease the production of this peptide and some of them are as follows (Annu Rev Pharmacol Toxicol. 2003, 43:545-84; J Clin Invest. 2003, 111:11-18):

a) Inhibition of β- or γ-secretase by small molecular weight compounds
b) Removal of Aβ42 peptides by designing active or passive vaccines to this peptide
c) preventing Aβ42 aggregation and toxicity by small molecule agents Niacin (Nicotinic acid) has been used for decades to treat hyperlipidemia. In particular its ability to raise the plasma HDL cholesterol levels has led to an increase in its pharmacological use (See Am J Cardiol. 2007, 100 (11A):S53-61). Niacin also has modest effects on triglycerides and LDL cholesterol. The clinical use of niacin is somewhat limited due to harmless but unpleasant side effect, a cutaneous flushing phenomenon which causes skin redness and itching. Nevertheless niacin currently remains to be the only agent on the market shown to definitely raise plasma HDL.

Niacin has been well known as a vitamin (vitamin B3) and used as drug or nutritional supplement for pellagra. However, phenolic ester hybrids of niacin or cocrystals of such hybrids with cocrystal formers like eugenol and oxalic acid or physical combination of niacin with other small molecule potentiating agents as pharmaceutical compositions for reduction of Aβ42 have not been disclosed previously.

While there is wealth of information on niacin's pharmacological effects on cholesterol and triglycerides, its use as a therapeutic for Alzheimer's has not been systematically studied. Specifically there is no prior art that reports the use of niacin alone or in combinations or niacin esters or cocrystals of niacin esters for reduction of Aβ42. There is one clinical study which reports that niacin consumption in the diet decreases the incidence of Alzheimer's (See J. Neurol Neurosurg Psychiatry, 2004, 75:1093-1099). However there is no mention in this study of how and why niacin could be having these effects. U.S. Pat. No. 4,336,258 relates to phenolic esters of eugenol and N-heteroarylcarboxylic acids, including nicotinic acid for use in stomatology drawing different utility for the combination. However, this patent neither discloses cocrystals of eugenol ester of niacin nor utility in Alzheimer's disease. Similarly, eugenol derivatives as potent lipoxygenase inhibitors has been disclosed in Sedeghian et al (See Biorganic and Med Chem. 2008, 16(2):890-91) for utility other than Alzheimer's disease. Also, effects of eugenol on the central nervous system has been disclosed by Yosifumi Irie (See Current Bioactive Compound, 2006, 2:57-66). However a combination of niacin and eugenol as a physical mixture or as an ester hybrid or as a cocrystal of the ester hybrid as a method to reduce Aβ42 and for treatment of Alzheimer's has hitherto not been disclosed.

There thus remains a need to conduct a systematic study of niacin alone or in combination with other small molecules to discover novel compositions endowed with a property of reducing Aβ42, its deposition, accumulation, and plaque formation and having therapeutic effect in treating Alzheimer's disease, dementia, and mild cognitive impairment.

SUMMARY OF THE INVENTION

The present invention provides (1) phenolic ester hybrids of niacin with m-methoxy-p-hydroxy phenyl compounds like eugenol, vanillin, apocynin, ferulic acid and eugenol epoxide and (2) cocrystals of hybrids as above, particularly cocrystal of niacin-eugenol hybrid with co-former like eugenol and oxalic acid (3) novel pharmaceutical compositions comprising a combination of niacin and one or more small molecule/potentiating agent like eugenol, curcumin, cinnamic acid, meclofenamic acid useful for the treatment of a disorder or a disease caused by excess production of amyloid beta peptide-42 (Aβ42), its deposition, accumulation, and plaque formation.

Amyloid beta peptide-42 (Aβ42) is the major pathogenic peptide which sets into motion a cascade of neurotoxic and pro-inflammatory events leading to development of Alzheimer's disease. The compounds and combinations presented herein are useful in the treatment of Alzheimer's disease (AD), dementia, and mild cognitive impairment as well as in other neurodegenerative disorders such as Parkinson's Disease and ischemic stroke.

The invention also provides a method of treatment of a human disorder or a disease condition with excess production of Aβ42, its deposition, accumulation, and plaque formation comprising administering therapeutically effective amount of compositions comprising niacin alone or in combination with one or more small molecule/potentiating agents or niacin ester hybrids or cocrystals of niacin ester hybrids that provide therapeutic effects in the treatment of a disorder and/or disease caused by excess production of Aβ42, its deposition, accumulation, and plaque formation. As per the invention, the said compositions are administered orally or parenterally.

This invention is further directed to a composition comprising therapeutically effective amount of niacin in combination with one or more small molecule/potentiating agent or niacin ester hybrids or cocrystals of niacin ester hybrids with at least one pharmaceutically acceptable carrier, diluent or excipient that provide therapeutic effects in the treatment of a disorder and/or disease caused by excess production of amyloid beta peptide-42 (Aβ42), its deposition, accumulation, and plaque formation.

The invention further provides pro-drugs of niacin which can exert desired pharmacological effect as the parent drug. These pro-drugs include carbonates, esters, amides, carbamates, mannich bases, oximes, imines, ethers, phosphates and the likes thereof.

The present invention is also directed to the use of a composition comprising therapeutically effective amount of niacin in combination with one or more small molecule/potentiating agent, niacin ester hybrids or cocrystals of niacin ester hybrids in the treatment of AD, dementia, and mild cognitive impairment as well as other neurodegenerative diseases such as Parkinson's Disease and ischemic stroke.

In summary, the present invention provides the following aspects:

In one aspect the invention provides niacin-eugenol/eugenol cocrystal, pharmaceutical compositions containing the cocrystal, and their use in the treatment of a disorder and/or a disease caused by excess production of Aβ42, its deposition, accumulation, and plaque formation. The cocrystals of the invention is used in the treatment of AD, dementia and mild cognitive impairments and other neurodegenerative disorders such as Parkinson's Disease and ischemic stroke.

In another aspect the invention provides hybrid series comprising niacin-vanillin, niacin-apocynin, niacin-ferulic acid, niacin-dihydro eugenol, niacin-eugenol epoxide, and niacin-isoferulic acid, pharmaceutical compositions containing them and their use in the treatment of a disorder or a disease caused by excess production of Aβ42, its deposition, accumulation, and plaque formation. The pharmaceutical compositions containing these hybrids are used in the treatment of AD, dementia and mild cognitive impairments and other neurodegenerative disorders such as Parkinson's Disease and ischemic stroke.

In yet another aspect niacin-eugenol hybrid is provided for the treatment of a disorder or a disease caused by excess production of (Aβ42), its deposition, accumulation, and plaque formation including AD, dementia and mild cognitive impairment and other neurodegenerative disorders such as Parkinson's Disease and ischemic stroke.

In another aspect, the invention also encompasses a combination of niacin+eugenol, niacin+cinnamic acid, niacin+meclofenamic acid and niacin+curcumin as pharmaceutical compositions that provides synergistic effects in treatment of a disorder or a disease caused by excess production of Aβ42, its deposition, accumulation, and plaque formation including AD, dementia, and mild cognitive impairment and other neurodegenerative disorders such as Parkinson's Disease and ischemic stroke.

BRIEF DESCRIPTION OF THE DRAWINGS

FIGS. 1 through 7 demonstrate inhibition of Aβ42 production by the novel combinations of niacin with other small molecules/potentiating agents as well as efficacy in animal models of disease.

DETAILED DESCRIPTION OF PRESENT INVENTION

The present invention discloses the therapeutic effects of (1) niacin esters with m-methoxy-p-hydroxy phenyl compounds like eugenol, vanillin, apocynin, ferulic acid and eugenol epoxide and (2) cocrystals of hybrids as above, particularly cocrystal of niacin-eugenol hybrid with cocrystal former like eugenol and oxalic acid (3) novel pharmaceutical compositions comprising a physical combination of niacin and one or more small molecule/potentiating agent like eugenol, curcumin, cinnamic acid, meclofenamic acid in treatment of Alzheimer's disease.

Niacin, also known as nicotinic acid, is pyridine-3-carboxylic acid which is well known as vitamin B3 and for its therapeutic uses. On reaction with alcohols, niacin gives rise to its esters. It also forms phenolic esters by reacting with phenolic compounds. Eugenol, also a natural product having anti-oxidant and anti-inflammatory properties is well known for its use in dentistry.

In one embodiment, the present invention provides a combination of niacin and eugenol in near stoichiometric ratio which exhibits a remarkable property of reduction of Aβ42 production in in vitro cell-based assays. Although niacin itself is active in this assay, eugenol is found to have a synergistic effect. Aβ42 is a major target for Alzheimer's Disease (AD) and therefore, the present invention provides a novel combination of niacin and eugenol for use in the treatment of AD. In addition, a few other potentiating agents like curcumin, cinnamic acid, meclofenamic acid have also shown such synergy with niacin which is encompassed in this invention.

In another embodiment, niacin and the potentiating agents are combined by covalent bonding. For example, reaction of niacin with eugenol, a phenolic natural compound having a m-methoxy-p-hydroxy phenyl motif (See Table 1), gave rise to the corresponding phenolic ester, namely eugenyl nicotinate (or eugenyl niacinate). In the present disclosure, the applicants refer to this niacin ester as niacin hybrid. As per the invention, a niacin hybrid comprises a phenolic ester of niacin. In a preferred embodiment, the niacin hybrids of the invention are detailed in Table 1. In a more preferred embodiment, niacin-eugenol hybrid which exhibited significant activity in the cell based assay for the treatment of AD is encompassed by the invention.

While niacin-eugenol hybrid (no. 1 in Table 1) has been a known composition of matter since 1947 (See Bull. Soc. Chim. Fr. 1947, 339-341), its therapeutic properties, notably in the field of stomatology, have been reported only in late seventies/early eighties (See U.S. Pat. No. 4,336,258). However, there has been no disclosure of its activity in Aβ42 assay or its potential use in the therapy of AD.

In another embodiment, the invention provides novel hybrids between niacin and m-methoxy-p-hydroxy phenyl compounds which includes but not limited to vanillin, apocynin, ferulic acid, dihydroeugenol, eugenol epoxide. Like eugenol, the first three compounds in this series are naturally occurring molecules while the last two are eugenol-derived. Even isoferulic acid, a m-hydroxy-p-methoxy isomer of ferulic acid has formed a hybrid with niacin. And some of these hybrids (See Table 1) have exhibited activity in Aβ42 assay and are therefore presented herein as novel therapeutics for AD, dementia and mild cognitive impairment. None of these hybrids has been hitherto reported nor have any of these been disclosed for use in therapy for AD. dementia and. mild cognitive impairment.

In addition to niacin-eugenol hybrid, the invention also provides cocrystals of this hybrid with eugenol as such, and with other cocrystal formers like oxalic acid have been prepared and evaluated for their activity for the first time. The applicant notes that the cocrystal of niacin-eugenol hybrid with eugenol has exhibited superior PK parameters (Example 9) and activity profile compared to niacin+eugenol combination or niacin-eugenol hybrid. This cocrystal designated as niacin-eugenol/eugenol cocrystal constitutes a novel composition useful in the treatment of AD, dementia and mild cognitive impairment associated with excess production of Aβ42, its deposition, accumulation, and plaque formation as well as other neurodegenerative diseases like Parkinson's Disease and ischemic stroke.

TABLE 1

Niacin ester hybrid [Niacin + mMpH (m-Methoxy-p-Hydroxy) compounds]

| No | Niacin + mMpH compound | Reaction structure |
|----|------------------------|--------------------|
| 1 | Niacin + Eugenol | Niacin $C_6H_5NO_2$ (123.11) + Eugenol $C_{10}H_{12}O_2$ (164.2) → $C_{16}H_{15}NO_3$ (269.30) |

TABLE 1-continued

Niacin ester hybrid [Niacin + mMpH (m-Methoxy-p-Hydroxy) compounds]

| No | Niacin + mMpH compound | Reaction structure |
|----|------------------------|--------------------|
| 2 | Niacin + Vanillin | Niacin $C_6H_5NO_2(123.11)$ + Vanillin $C_8H_8O_3(139.13)$ → $C_{14}H_{11}NO_4(257.24)$ |
| 3 | Niacin + Apocynin | Niacin $C_6H_5NO_2(123.11)$ + Apocynin $C_9H_{10}O_3$ → $C_{15}H_{13}NO_4(271.27)$ |
| 4 | Niacin + Ferulic acid | Niacin $C_6H_5NO_2(123.11)$ + Ferulic acid $C_{10}H_{10}O_4(194.18)$ → $C_{16}H_{13}NO_5(299.28)$ |
| 5 | Niacin + Eugenol Epoxide | Niacin $C_6H_5NO_2(123.11)$ + Eugenol epoxide $C_{10}H_{12}O_3(180.20)$ → $C_{16}H_{15}NO_4(285.29)$ |
| 6 | Niacin + Isoferulic acid | Niacin $C_6H_5NO_2(123.11)$ + Ferulic acid $C_{10}H_{10}O_4(194.18)$ → $C_{16}H_{13}NO_5(299.28)$ |

The present invention thus includes but not limited to the following niacin esters: niacin-eugenol hybrid, niacin-vanillin hybrid, niacin-apocynin hybrid, niacin-ferulic acid hybrid, niacin-isofreulic acid hybrid, niacin-dihydroeugenol hybrid and niacin eugenol epoxide hybrid. These hybrids have been synthesized and tested for their effects on the production of Aβ42 in a cell-based assay. All these hybrids were found to be active in reducing the production of Aβ42, with the niacin-eugenol hybrid being the most active among the series.

The present invention also includes but not limited to the following cocrystals: niacin-eugenol hybrid co-crystallised with eugenol, niacin-eugenol hybrid co-crystallized with oxalic acid dihydrate. These are denoted as niacin-eugenol/eugenol cocrystal and niacin-eugenol/oxalic acid dihydrate cocrystal respectively. Applicant has tested these in Aβ42 assay and found that niacin-eugenol/eugenol cocrystal exhibited impressive activity.

It should also be noted that a novel combination of niacin with eugenol, cinnamic acid, meclofenamic acid or curcumin has been shown to have synergistic effect in inhibiting Aβ42 production. In the present invention, applicant has tested the effects of niacin by itself and in combination with other agents on the production of Aβ42 by human neuroblastoma SH-SY5Y cells. Applicant deliberately did not use the often used artificially transfected cell lines that have massive over expression of mutated form of APP and tend to exaggerate the inhibitory effects of compounds. Secondly by using a non-transfected native cell line we would preserve all the indigenous machinery for Aβ42 production.

Since niacin is a powerful lipid lowering agent in animals and humans, this plasma lipid effects of niacin could confound the exact mechanism of niacin's effects on production of Aβ42 in whole animal studies. To completely eliminate any contribution of plasma lipid lowering effects of niacin, applicants used a direct cell based model described above of Aβ42 reduction where the compound is added to SH-SY5Y human neuronal cells in isolation.

Aβ42 production can be controlled by many pathways and mechanisms such as secretase enzyme activity inhibition, down regulation of APP or secretase gene expression. This means that the best strategy to maximally impact Aβ42 will be to affect multiple pathways at the same time. Since AD is a disease of the elderly, it is imperative that the drugs used have high safety margins. One way to achieve this is to use drugs/agents with known safety records such as natural products like curcumin, eugenol and cinnamic acid. Therefore, applicants used niacin in combination with these drugs/agents to analyze its additive or/and synergistic effects in lowering the production of Aβ42.

In the present invention, applicants demonstrate, for the first time, that niacin is a strong inhibitor of Aβ42 production by the neuronal cells. Since this is observed in an isolated cell system, this effect cannot be related to plasma lipid lowering changes. Furthermore applicants also demonstrate that in combination with some other agents there is an unexpected potentiation in niacin's ability to reduce production of Aβ42. Combination therapy has two distinct advantages relative to mono therapy: a) combination allows lower doses of each of the drugs to be used versus when they are used singly, thus limiting any side effects and b) combination therapy is likely to be more efficacious because of possibility of working thru more than one mechanistic pathway. Together these results support the use of niacin alone or in combination as a therapy for AD.

The compounds used in the present invention may have asymmetric centres and occur as racemates, recemic mixtures, and as individual diastereomers, with all possible isomers being included in the present invention. The composition of the present invention can be administered in standard forms adapted to the method of administration chosen, for example via the oral or parenteral routes. For example, it is possible to use formulations of tablets or capsules or emulsions or solutions.

The weight ratios between niacin and small molecule/potentiating agent may be comprised between 1:1 and 1:50.
Definitions Niacin referred in the present invention includes niacin and niacin derivative having the basic niacin frame work.

Niacin ester hybrids as used in the present invention means phenolic esters of niacin with m-methoxy-p-hydroxy phenyl compounds like eugenol, vanillin, apocynin, ferulic acid, dihydroeugenol, eugenol epoxide and m-hydroxy-p-methoxy phenyl compounds like isoferulic acid. These are denoted, respectively as niacin-eugenol hybrid, niacin-vanillin hybrid, niacin-apocyninn hybrid etc. (See Table 1).

Niacin cocrystal as mentioned in the present invention means the product of cocrystallization of niacin-eugenol hybrid with a cocrystal former like eugenol itself or oxalic acid dihydrate gives rise to the cocrystals designated as niacin-eugenol/eugenol cocrystal or niacin-eugenol/oxalic acid dihydrate cocrystal receptively. The cocrystals so produced were characterized by physico-chemical, spectroscopic and powder X-ray Crystallographic data.

Cocrystal former as mentioned in the present invention means a small molecule agent or a neutraceutical effective in forming cocrystals with niacin ester hybrids Small molecule refers to organic chemical compounds having molecular weight of about 800 and may be present in the form of salts. Potentiating agent refers to the substance or agent that enhance the therapeutic effect of niacin. According to the invention, small molecule/potentiating agent include but are not limited to eugenol, curcumin, cinnamic acid or meclofenamic acid and the likes thereof.

Salts of the compounds of this invention include the conventional non toxic salts of the compounds presented which can be readily recognized by a person skilled in the art e.g., salts derived from inorganic or organic bases and organic or inorganic acids and the likes thereof.

Pro-drugs of the present invention refer to bio-reversible derivatives of niacin that undergo an enzymatic and/or chemical transformation in vivo to release the active parent drug, which can exert desired pharmacological effect. Such pro-drugs include carbonates, esters, amides, carbamates, mannich bases, oximes, imines, ethers, phosphates and the likes thereof.

A disease or a disorder characterized by excess production of amyloid beta peptide 42 (Aβ42) typically encompasses Alzheimer's disease (AD), dementia and mild cognitive impairment or other neurodegenrative diseases such as Parkinsons's disease and ischemic stroke and all of the aforementioned conditions are encompassed in the present invention.

The methods, examples and FIGS. 1-7 given below demonstrate the enhanced response in the reduction of Aβ42 levels and their therapeutic effects by the compositions of the present invention. The invention is further illustrated by the following methods and non-limiting examples.
Methods
Human Neuronal Cell Model:

We used the human Neuroblastoma SH-SY5Y cells for drug testing as a model for Aβ42 production. The cells were cultured in Dulbecco's modified Eagle's medium or Dulbecco's modified Eagle's medium/Ham's F-12 medium supplemented with 10% fetal bovine serum, 100 units/ml penicillin, and 100 μg/ml streptomycin in a humidified atmosphere of 95% air, 5% $CO_2$ at 37° C. as per suppliers instructions. Cells were typically incubated with the compounds overnight and then, media was harvested for Aβ42 quantitation as described below. Cell toxicity was monitored using the MTT assay and all data reported are corrected for any cell loss.
Sandwich Enzyme-linked Immunosorbent Assay (sELISA) for Quantization of Aβ42:

The capture antibody, detection antibody and secondary antibody as well as standard purified preparations of Aβ42 were obtained from Sigma-Aldrich. Cells were cultured for 24 h in the presence or absence of compounds and the conditioned medium was subjected to sELISA.

In Vivo Pharmacokinetics of Niacin-eugenol Hybrid Cocrystal:

In vivo pharmacokinetic (PK) studies were conducted in male Swiss Albino mice. Niacin-Eugenol physical mixture or Niacin-Eugenol hybrid cocrystal was administered to the animals at a dose of 0.73 mmol/kg orally (n=2 mice per time point). Blood samples (approx. 0.2 mL) were withdrawn from the animals at 0, 0.5, 2, 4, 6 and 24 hr post administration. Plasma was separated by centrifugation at 4000 rpm for 10 minutes and stored in ice for analysis. Animals were sacrificed at the above time points; and brains were excised, snap frozen in liquid nitrogen and stored at −80° C. Samples were analyzed by high-performance liquid chromatography (HPLC) with UV detection. Briefly, 50 μL acetonitrile was added to 50 μL of plasma to precipitate the plasma proteins. The precipitated proteins were removed by centrifugation at 15000 rpm at 5° C. for 10 min. The supernatant was collected in HPLC vials and kept at 4° C. for analysis.

200 mg of the brain tissue was homogenized in Acetonitrile. The resultant homogenate was centrifuged at 15000 rpm for 10 minutes at 4° C. 40 μL of the supernatant was taken for HPLC analysis. Pharmacokinetic parameters were calculated using WinNonLin v5.2 software. The plasma and brain samples were analyzed for Niacin and Eugenol concentrations using HPLC under the conditions shown below:

| | |
|---|---|
| Mobile phase | 0.1% Formic acid in Milli-Q water:Acetonitrile = 30:70 |
| Column | Inertsil ODS-3V 5 μm, 4.6 × 150 mm |
| Flow rate | 0.5 mL/min |
| λmax | 272 nm |
| Retention time | Niacin = 3.2 min, Eugenol = 5.8 min, hybrid = 7.8 min |

Testing of Cocrystal in a Human APP Overexpressing *Drosophila* Transgenic Model:

The effect of cocrystal of niacin-eugenol/eugenol was tested in a *drosophila* model which over expresses the human APP protein. The creation of the APP over expressing flies and other methods for these studies are as described previously by Greeve et al (See J. Neuroscience, 2004, 24:3899-3906). The targeted over/ectopic expression of APP in the brain using UAS promoter driven APP transgene, induced by a specific GAL4 trans-driver in the *Drosophila* model system was used. Adult flies, a total of 80 flies (4 males and 4 females per tube, 10 tubes) were fed right after their emergence and the survival was examined until the end of 9th day. The drugs to be tested were delivered with the food.

Testing of Cocrystal on Scopolamine Induced Memory Deficit in Novel Object Recognition Task in Wistar Rats:

The effect of cocrystal is tested in a rat cognition model often used to test improvements in cognition, namely the scopolamine induced memory deficit in novel object recognition task. Male rats are administered with vehicle or test compounds (donezepil at or cocrystal at 10, 30 or 100 mg/kg body weight for 7 days before the initiation of habituation and continued through out the novel object recognition task experimentation period.

The test will be conducted as follows: On day 1 the rats will be acclimatized for 20 min to their respective arenas (one hour after administering with vehicle or test compounds) and then returned to their respective home cages. On day 2 the rats will be administered vehicle or test compound one hour prior to trial. Donepezil will be administered once, 30 minutes prior to familiarization phase. Scopolamine (1 mg/kg, i.p.) will be injected 20 min prior to trial. 20 min after scopolamine administration, rats will be subjected to familiarization phase. Handling will be done by individually placing the animals on the palm of the hand for 10 to 15 sec before placing it into arena. During the familiarization phase rats will be allowed to explore for 3 min the arenas containing two similar objects (familiar objects, plastic bottles, 12 cm high×5 cm diameter) covered with yellow masking tape. The time spent investigating each of the identical objects will be recorded by an investigator (blind to the treatment) using hand held stopwatches. All the trials will be video recorded. Investigation of the objects is defined as smelling, sniffing, licking, nose within 1 cm radius of the object with moving vibrissae, touching the object with fore paw having nose directed towards the object. After the trial is completed animals will be returned to their home cages. After an inter trial interval of 3 min the rats will be subjected to choice trial for a period of 3 min. Here the rats will be allowed to explore the arena, which contains a copy of the familiar object and a novel object (amber color glass bottle, 11.5 cm high×4.5 cm diameter). The time spent investigating the novel and familiar objects will be recorded by the same investigator (investigator who scored familiarization phase and blind to the treatment) using hand held stopwatches. Exploration of each animal will be recorded on the DVD recorder using a camera held above the arena. Animals, which show the exploration of greater than or equal to 15 sec during the familiarization trial and 10 sec during the choice trail, will be considered in the data analysis. This is to ensure that the animals received object training. The animal that shows selective exploration (defined as exploration of one object 20 seconds more than the other object in familiarization phase) will not be considered for data analysis. The novel object recognition task experimentation will be carried out over a period of 4 days i.e. first 6 animals will be experimented on first two days and the next 6 animals will be experimented on next 2 days (The 7 day dosing schedule will be initiated accordingly such that all animals receive 7 doses of vehicle or test drug before the day of habituation. Totally each animal would receive 9 doses of vehicle or test drug).

Statistical analysis: For each treatment group, the time spent with the novel and familiar objects will be compared by Student's paired 't' test. The discriminative index for the drug treated groups will be compared to that of the vehicle group by use of the Kruskal-Wallis test. The discriminative index is ratio of time spent exploring the novel object divided by sum of time spent exploring the novel object and familiar object in choice trial. Outliers based on discriminative index (Grubbs outlier test (or) greater or less than two standard deviation from mean) will not be considered for statistical analysis.

EXAMPLES

Figure 1:
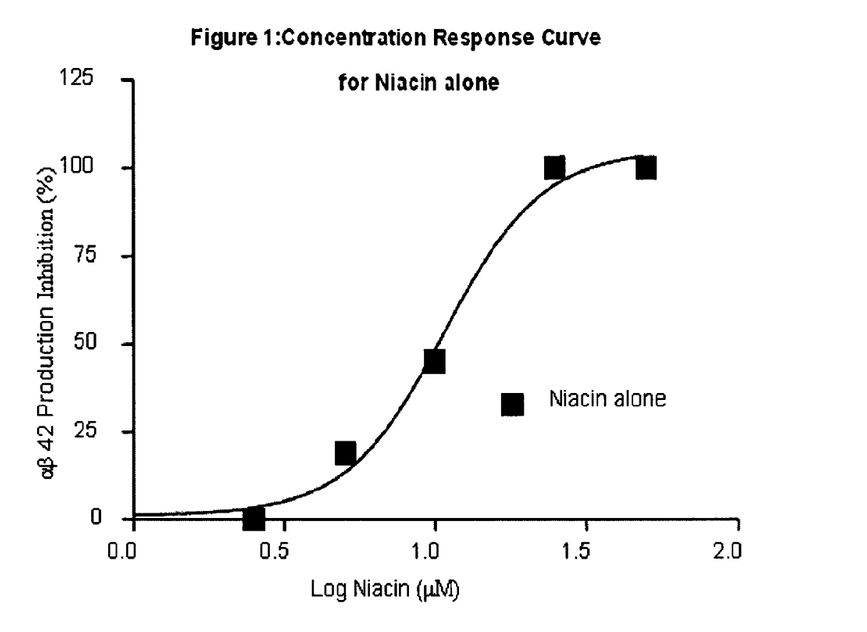
FIG. 1: Concentration Response Curve for Niacin alone.

1) Dose dependent reduction of Aβ42 production by niacin in human neuronal SH-SY5Y cells: Cells were incubated overnight with either no niacin or with increasing concentrations of niacin. The cell media was then harvested and Aβ42 in the media was quantitated using sandwich ELISA. As shown in FIG. 1, there was a concentration dependent inhibitory effect of niacin on Aβ42 levels in the media. While lower concentrations of up to 2.5 μM niacin had little effect, there was good effect at 5 and 10 μM and there was robust inhibitory effect at 25 and 50 μM niacin which inhibited by 100%. A calculated IC50 of niacin's inhibitory effect was 10.6 μM. These results show that niacin is a potent inhibitor of Aβ42 production in this cell-based model.

Figure 2:
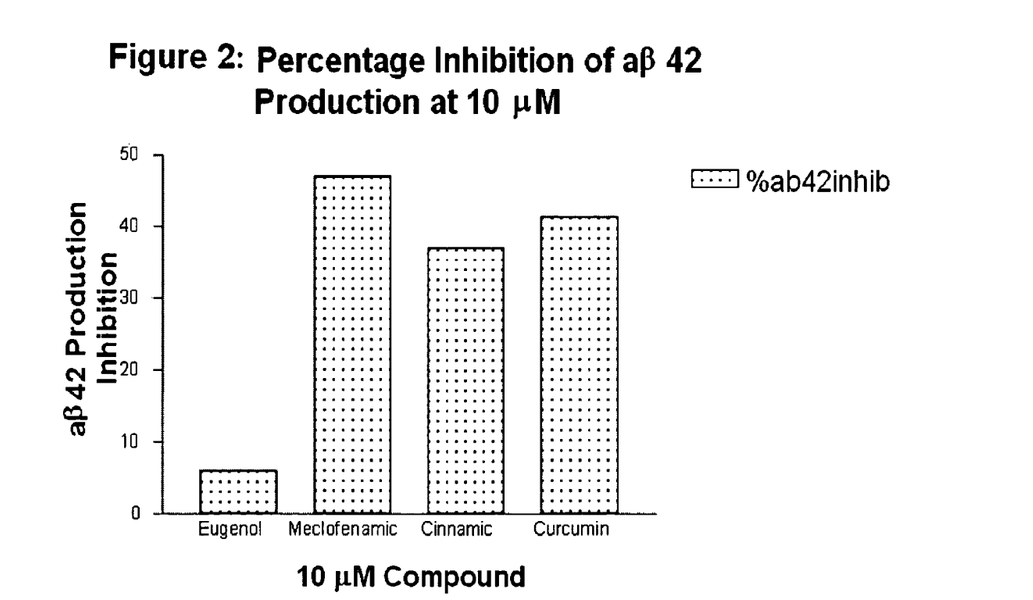
FIG. 2: Percentage inhibition of Aβ42 production at 10 μM concentration by eugenol, meclofenamic acid, cinnamic acid and curcumin.

2) Curcumin, Meclofenamic acid, eugenol and cinnamic acid reduce Aβ42 production by SH-SY5Y cells: The effects of 10 µM of eugenol, curcumin, cinnamic acid and Meclofenamic acid on Aβ42 production were examined. All of the agents inhibited the Aβ42 production by varying degrees up to 48% (FIG. 2). These data show that the compounds have inhibitory capability. Importantly this provides a strong basis for combining any of these agents with niacin to potentiate niacin's effects.

Figure 3:
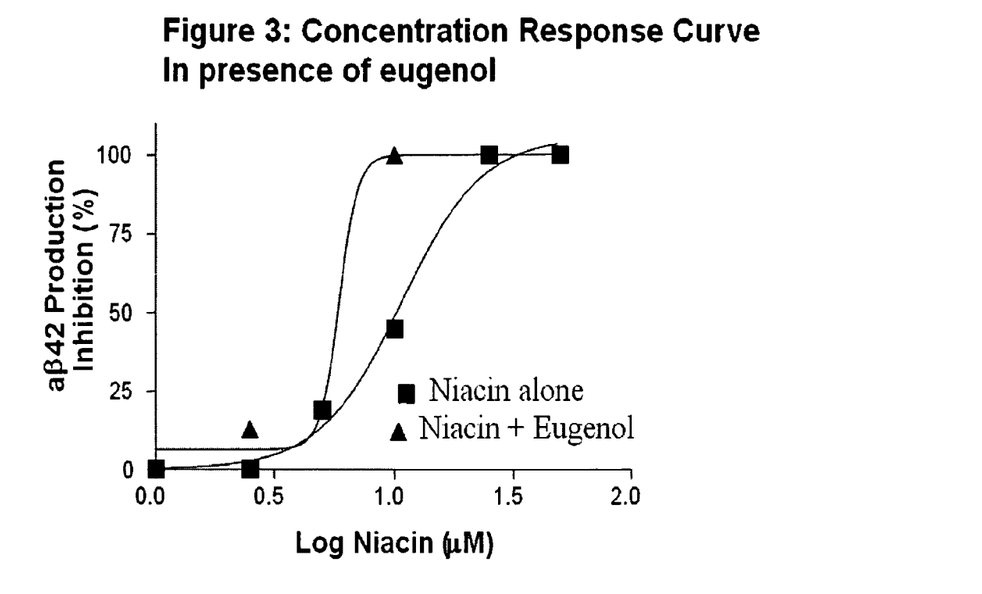
FIG. 3: Concentration Response Curve in presence of eugenol.

3) Combination of eugenol and niacin enhances niacin's inhibitory effect on Aβ42 production: Varying concentrations of niacin were tested in the presence of 5 µM of eugenol to explore its ability to potentiate niacin's effect. As shown in FIG. 3, the inhibitory curve for niacin shifted to the left in the presence of eugenol suggesting that eugenol was able to enhance niacin's inhibitory effects. This was shown clearly by calculating IC50 of niacin in the presence or absence of eugenol, niacin alone has an IC50 of about 10.6 µM where as in the presence of eugenol its IC50 was lowered to 5.9 µM, a reduction of about 45%. These data show that niacin can be combined with eugenol to a) enhance its activity and b) to reduce the amount (IC50) of niacin required for inhibition.

Figure 4:
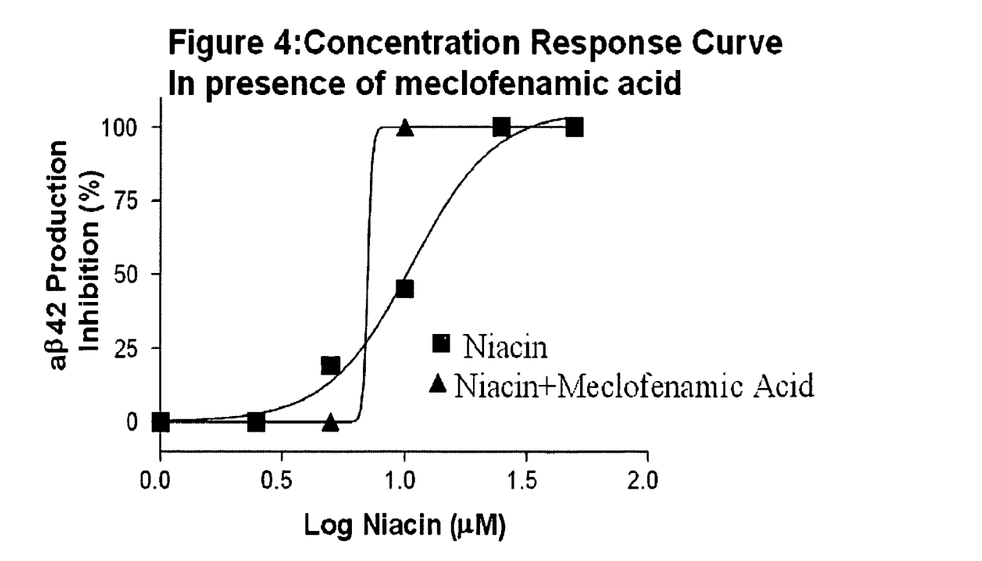
FIG. 4: Concentration Response Curve in presence of meclofenamic acid.

4) Combination of Meclofenamic acid and niacin enhances niacin's inhibitory effect on Aβ42 production: Varying concentrations of niacin were tested in the presence 5 µM of Meclofenamic acid to explore its ability to potentiate niacin's effect. As shown in FIG. 4, the inhibitory curve for niacin shifted to the left in the presence of meclofenamic acid suggesting that it was able to enhance niacin's inhibitory effects. This was shown clearly by calculating IC50 of niacin in the presence or absence of meclofenamic acid, niacin alone has an IC50 of about 10.6 µM where as in the presence of meclofenamic acid its IC50 was lowered to 7 µM, a reduction of about 33%. These data show that niacin can be combined with meclofenamic acid to a) enhance its activity and b) to reduce the amount (IC50) of niacin required for inhibition. There is an additional benefit to combining niacin with meclofenamic acid; it could also reduce the flushing that may by caused niacin in addition to adding to its efficacy.

Figure 5:
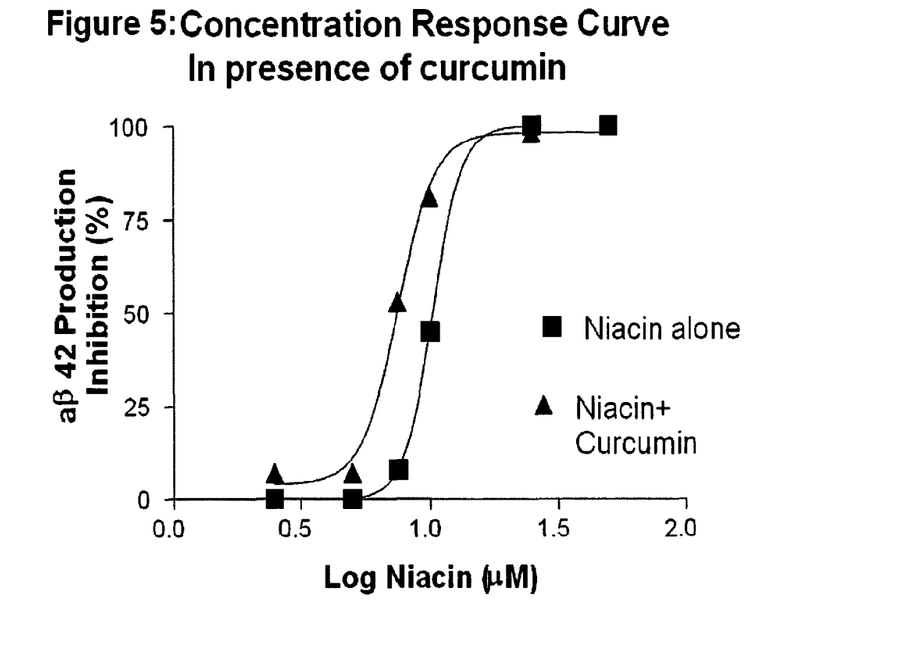
FIG. 5: Concentration Response Curve in presence of curcumin.

5) Combination of niacin and curcumin reduces Aβ42 production: Varying concentrations of niacin were tested in the presence 5 µM of curcumin to explore its ability to potentiate niacin's effect. As shown in FIG. 5, the inhibitory curve for niacin shifted to the left in the presence of curcumin suggesting that curcumin was able to enhance niacin's inhibitory effects. This was shown clearly by calculating IC50 of niacin in the presence or absence of curcumin, niacin alone has an IC50 of about 10.25 µM where as in the presence of curcumin its IC50 was lowered to 7.5 µM, a reduction of about 27%. These data show that niacin can be combined with curcumin to a) enhance its activity and b) to reduce the amount (IC50) of niacin required for inhibition.

Figure 6:
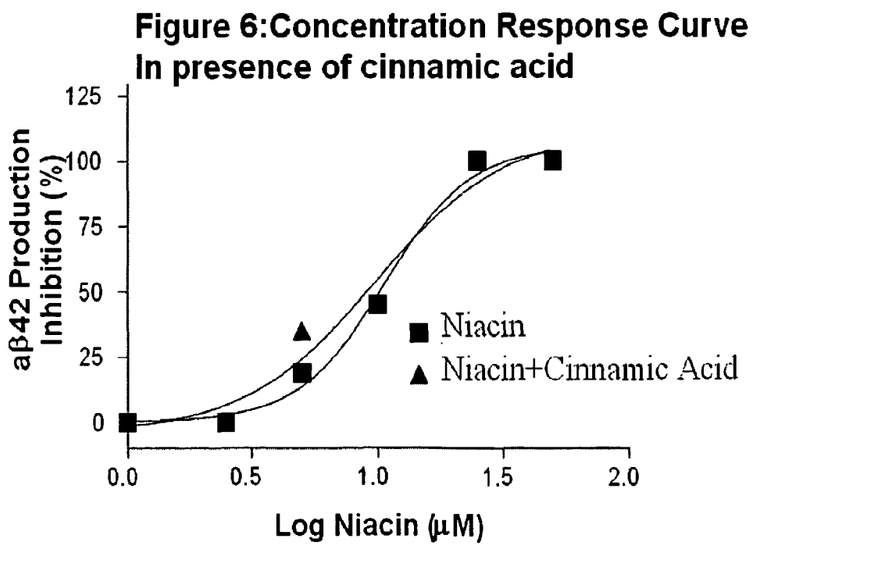
FIG. 6: Concentration Response Curve in presence of cinnamic acid.

6) Combination of cinnamic acid and niacin reduces Aβ42 production: Varying concentrations of niacin were tested in the presence 5 µM of cinnamic acid to explore its ability to potentiate niacin's effect. The inhibitory curve for niacin was augmented in the presence of cinnamic acid (FIG. 6). Niacin alone showed an IC50 of about 10.6 µM whereas in the presence of cinnamic acid its IC50 was lowered to 9.8 µM, amounting to a reduction of about 15%. These data show that niacin can be combined with cinnamic acid to enhance its activity.

7) Structure Activity Relationship of Niacin Based Compounds:

Since niacin and eugenol combinations were very active at blocking the secretion of Aβ42, we then covalently linked niacin to eugenol through ester bond and tested its activity. This covalently linked niacin-eugenol hybrid was also active at blocking Aβ42 secretion with an IC50 of 14 µM. In addition, several other niacin ester hybrid compounds were synthesized as shown below in Table 2.

TABLE 2

Effect of niacin ester hybrids in blocking Aβ42 secretion

| Niacin ester hybrids | IC50 (µM) in cell based abeta assay |
| --- | --- |
| Niacin-eugenol hybrid | 14.0 |
| Niacin-vanillin hybrid | 44.6 |
| Niacin-apocynin hybrid | 25.3 |
| Niacin-ferulic acid hybrid | >50 |
| Niacin-isofreulic acid hybrid | 36.8 |
| Niacin-dihydro eugenol hybrid | >50 |
| Niacin-eugenol epoxide hybrid | 17.5 |

While several of the hybrid compounds were active, the most potent hybrid compound continued to be niacin-eugenol ester linked hybrid.

By way of example, preparation of some of the above mentioned hybrids are provided herein:

a. Preparation of Nicotinic acid 4-allyl-2-methoxy phenyl ester (Niacin-Eugenol Hybrid)

To a solution of Niacin 1 (1.6 g, 13.1 mmol) in dichloromethane (DCM, 10 mL) was added Eugenol 2 (2 g, 13.1 mmol), N-methyl morpholine (NMM, 4.3 mL, 39 mmol) and EDCl.HCl (5 g, 26.2 mmol). The resulting mixture was stirred at ambient temperature (25-27° C.) for 3 h and it was diluted with water, then extracted with dichloromethane and the organic layer dried over anhydrous sodium sulfate. It was then concentrated and chromatographed over a column of silica gel using petroleum ether:ethyl acetate to afford the title compound 3 as a colorless solid (300 mg, 8.5%, mp (° C.): 72-74) $^1$H NMR (300 MHz, CDCl$_3$); ☐ 9.43 (s, 1H), 8.88 (s, 1H), 8.53 (d, J=6 Hz, 1H), 7.53 (dd, J=5 & 8 Hz, 1H), 7.07 (d, J=8.4 Hz, 1H), 6.85 (s, 1H), 6.82 (s, 1H), 5.99 (m, 1H), 5.14 (m, 2H), 3.83 (s, 3H), 3.44 (d, J=6.6 Hz, 1H); LCMS (m/z): 269.7 (M+1); HPLC: $t_{Ret}$: 5.43 (99.7%).

b. Preparation of Nicotinic acid 4-formyl-2-methoxy-phenyl ester (Niacin-Vanillin hybrid)

To a solution of Niacin 1 (1.6 g, 13.1 mmol) in dichloromethane (10 mL) was added Vanillin 8 (2 g, 13.1 mmol), N-methyl morpholine (4.3 mL, 39 mmol) and EDCl.HCl (5 g, 26.2 mmol). The resulting mixture was stirred at ambient temp for 3 h. It was then diluted with water, extracted with dichloromethane, and the organic layer dried over anhydrous sodium sulfate and concentrated. The crude product thus obtained was then chromatographed using over a column of silica gel using petroleum ether:ethyl acetate (1:1) to afford the title compound as a off white solid (300 mg, 9%, mp (° C.): 92-94) $^1$H NMR (300 MHz, DMSO-D6): ☐ 10.02 (s, 1H), 9.25 (d, J=2 Hz, 1H), 8.93 (dd, J=5 & 1.5 Hz, 1H), 8.48 (dt, J=1.8 Hz & 8 Hz, 1H), 7.67 (m, 3H), 7.57 (d, J=8 Hz, 1H), 3.87 (s, 3H)); LCMS (m/z): 257.7 (M+1); HPLC: $t_{Ret}$: 6.486 (98.9%).

Other hybrids mentioned in Table 1 were prepared in similar fashion.

8) Cocrystal formation of niacin-eugenol hybrid with eugenol: In order to further improve the physicochemical characteristics and PK profile of the niacin-eugenol hybrid, a cocrystal of this compound with eugenol was developed.

a) Cocrystal of Eugenolnicotinate with Eugenol

EUGENOL NICOTINATE

EUGENOL

Method of Preparation:

Experiment for cocrystal formation was carried out by refluxing Eugenolnicotinate and cocrystal former in 1:1 molar ratio (26.9 mg of Eugenolnicotinate+15.4 μL of Eugenol), in DMSO at 150° C. for one hour and the mixture was left for slow evaporation. The resultant crystals were spectrally characterized.

Spectral Data:

Comparison of IR Data:

| Eugenolnicotinate IR (cm$^{-1}$) | Cocrystal former IR (cm$^{-1}$) | Cocrystal IR (cm$^{-1}$) |
|---|---|---|
| 3068, 3022, 1740, 1591, 1508, 1281 | 3524, 1513 1267, 1234 | 3023, 2977, 2942, 2899, 2167 1740, 1711, 1508, 1416 1283, 1084, 1027 |

Comparison of PXRD Data:

| Eugenolnicotinate (2 Theta) | Cocrystal former (2 Theta) | Cocrystal (2 Theta) |
|---|---|---|
| 16.1, 17.7, 18.3, 21.2, 24.9, 25.8, 27.3 | — | 7.2, 7.5, 12.2, 12.7, 17.3, 18.3, 24.4, 25.8, 26.1, 28.4 |

Melting Point Data:

| Eugenolnicotinate | Cocrystal former | Cocrystal |
|---|---|---|
| 77.5-78.5° C. | — | 67-70° C. | b) Cocrystal of Eugenolnicotinate with Oxalic Acid Dihydrate

EUGENOL NICOTINATE

Method of Preparation:

Experiment for cocrystal formation was carried out by solvent (Methanol) assisted grinding of Eugenolnicotinate with cocrystal former in 1:1 molar ratio (26.9 mg of Eugenolnicotinate+12.6 mg of oxalic acid), for 30 minutes. The resultant paste on grinding yields a hygroscopic solid.

Spectral Data:
Comparison of IR Data:

| Eugenolnicotinate IR (cm$^{-1}$) | Cocrystal former IR (cm$^{-1}$) | Cocrystal IR (cm$^{-1}$) |
|---|---|---|
| 3068, 3022, 1740, 1591, 1508, 1281 | 3412, 1680, 1265, 727 | 3425, 2577, 1949, 1749, 1713 1604, 1509, 1292 |

Comparison of PXRD Data:

| Eugenolnicotinate (2 Theta) | Cocrystal former (2 Theta) | Cocrystal (2 Theta) |
|---|---|---|
| 16.1, 17.7, 18.3, 21.2, 24.9, 25.8, 27.3 | | 14.6, 18.5, 25.6, 28.8, 30.2, 30.9 |

Comparison of Melting Point Data:

| Eugenolnicotinate | Cocrystal former | Cocrystal |
|---|---|---|
| 77.5-78.5° C. | 101-102° C. | 85-109° C. | c) The IC50 of the niacin-eugenol/eugenol cocrystal as determined in Aβ42 assay was 15.01 μM.

9) Pharmacokinetic Characterization of Niacin-eugenol Cocrystal:

The PK properties of the niacin-eugenol hybrid and niacin-eugenol/eugenol cocrystal were compared to that of a simple combination of niacin and eugenol. The PK parameters of the two preparations are shown below in Tables 3 and 4.

TABLE 3

| PK parameter For niacin | Niacin-eugenol combination Plasma | Niacin-eugenol combination Brain | Niacin-eugenol hybrid Plasma | Niacin-eugenol hybrid Brain | Niacin-eugenol/eugenol cocrystal Plasma | Niacin-eugenol/eugenol cocrystal Brain |
|---|---|---|---|---|---|---|
| $T_{max\ (hr)}$ | 0.25 | 0.25 | 1 | 1 | 0.5 | 0.5 |
| $C_{max\ (uM)}$ | 104 | 61 | 23 | 77 | 65 | 73 |
| $AUC_{(0-infinity)}$ hr * umol | 129 | 298 | 38 | 153 | 102 | 223 |
| $T_{1/2\ (hr)}$ | 0.4 | 1.1 | 0.6 | 0.8 | 0.9 | 1.1 |

TABLE 4

| PK parameter For eugenol | Niacin-eugenol combination Plasma | Niacin-eugenol combination Brain | Niacin-eugenol hybrid Plasma | Niacin-eugenol hybrid Brain | Niacin-eugenol/eugenol cocrystal Plasma | Niacin-eugenol/eugenol cocrystal Brain |
|---|---|---|---|---|---|---|
| $T_{max\ (hr)}$ | 0.25 | 0.25 | 0.25 | 1 | 0.25 | 0.25 |
| $C_{max\ (uM)}$ | 6 | 73 | 28 | 121 | 15 | 55 |
| $AUC_{(0-infinity)}$ hr * umol | 48 | 457 | 461 | 2256 | 2118 | 2041 |
| $T_{1/2\ (hr)}$ | >24 | >24 | 9.1 | 14 | >24 | >24 |

As shown in the above tables, there are differences in PK parameters between the cocrystal and niacin-eugenol hybrid as well as a combination of niacin and eugenol when compared at equimolar doses.

Differences in Niacin PK Parameters:
a) $T_{max}$ (hr): Compared to physical mixture the Tmax (time taken to reach maximum plasma and brain levels) was increased by 4-fold and 2-fold for hybrid and cocrystal respectively.

Differences in Eugenol PK Parameters:
a) $T_{max}$ (hr): There was a 4-fold increase in $T_{max}$ for eugenol in the brain with the hybrid compared to physical mixture
b) $C_{max}$ (μM): The $C_{max}$ values (maximum concentrations of drug reached) with hybrid was 65% increased compared to physical mixture in the brain and 4.6-fold increased in the plasma
c) $AUC_{infinity}$ (Area under the curve concentrations of drugs projected at time infinity such as may happen with chronic dosing. Higher values are indicative of higher drug levels)
   Combination versus hybrid: 9.6-fold and 4.9-fold increases in AUC infinity with hybrid in plasma and brain values respectively
   Combination versus cocrystal: 44-fold and 4.4-fold increases in AUC infinity in plasma and brain values respectively.
d) $T_{1/2}$ (hr): $T_{1/2}$ is the half-life of the drug and ideally, lower $T_{1/2}$ are preferred because they may limit drug accumulation. The $T_{1/2}$ of eugenol was reduced for the hybrid in both plasma and brain (9.1 and 14 in plasma and brain versus >24 for plasma and brain for physical mixture.

Collectively these data show that the hybrid and the cocrystal ester bonds are cleaved in vivo and generate sufficient levels of free niacin and eugenol in the brain (target tissue) and therefore act as pro-drugs. The data also show that there were improvements in selected PK parameters using the hybrid and the cocrystal.

10) Niacin-Eugenol Cocrystal Enhances Survivability in a Human APP Transgenic *Drosophila*:

The *drosophila* transgenic model has been frequently used to study neurodegenerative diseases such as alzheimer's and Parkinson's. Modeling human brain diseases in *Drosophila melanogaster* offers several advantages for investigation of molecular and cellular mechanisms underlying human disease (See Annu. Rev. Neurosci., 2003, 26:627-656 and Neuron, 2006, 52:169-178). Short life span, large number of offspring, many genetic techniques, a well known anatomical situation and a wide variety of mutants are convenient characteristics of *Drosophila* as a model organism. *Drosophila* models also have the advantage of speed, cost efficiency and the need for compound quantities required for testing are less. Time and tissue specific inducible promoters are available. In brain disease models, brain and the complex eye of adult *Drosophila* are often used as organs which are targeted and result in dysfunction. Especially the mushroom bodies, association areas necessary for olfactory learning and memory, composed of neurons with small, densely packed cell bodies, are relevant in brain disease.

Studies in *Drosophila* using the targeted expression of the key genes of AD, such as human APP, beta secretase and the presenilins lead to the generation of β-amyloid plaques and age-dependent neurodegeneration as well as to death, a shortened life span, and defects in wing vein development (Greeve et al, 2004). Therefore the effect of drugs on survival rates can be used as a measure of the drugs ability to impact neurodegeneration in such models.

Figure 7:
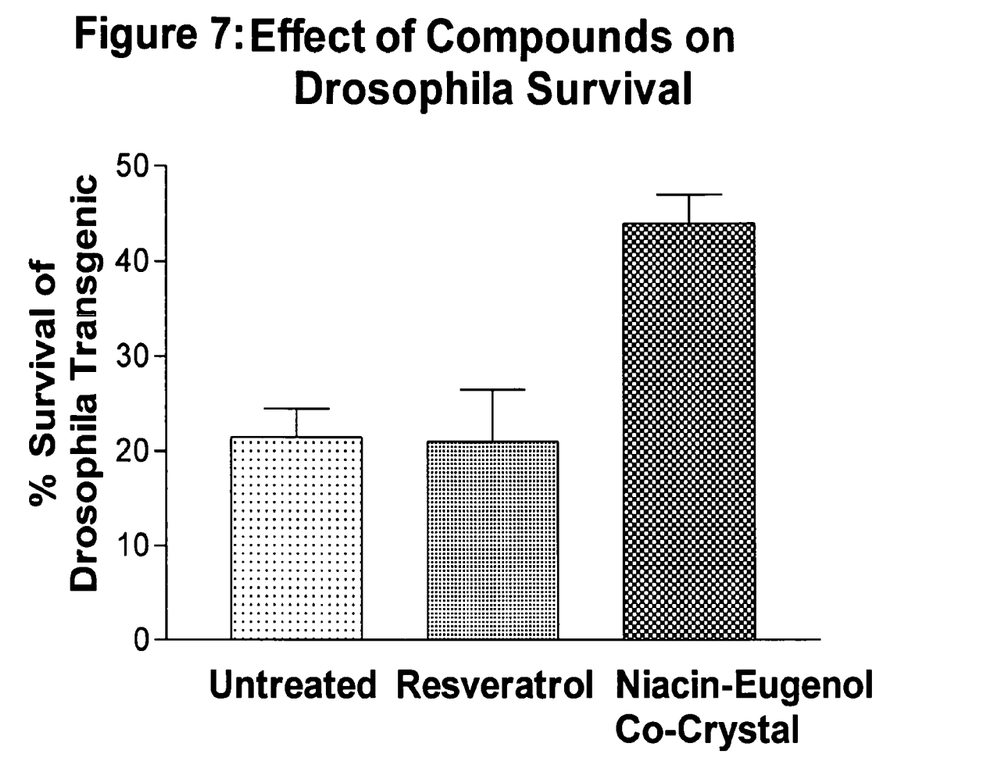
FIG. 7: Effect of niacin-eugenol cocrystal on survival of APP transgenic *drosophila*.

Beta secretase activity is not present in *Drosophila*, whereas γ-secretase, presenilin and nicastrin are conserved. Expression of human Aβ40 and Aβ42 in the fly brain caused age-dependent learning defects but only Aβ42 led to formation of diffuse amyloid deposits in the Kenyon cell region (See Proc. Natl. Acad. Sci. USA, 1998, 95:13703-13708). Expression of Aβ42 in the CNS was found to cause short-term memory impairment. Given the above knowledge and information available on the *drosophila* models, we were interested in examining the effects of the cocrystal in death due to neurodegeneration caused by human APP. We choose to test it in a simpler model rather than use double or triple transgenic models which over expresses human APP, beta secretase and presenilin since we do not expect our compounds to directly modulate the activity of either beta secretase or presenilin. We compared the effects on survival rates of human APP over expressing files of a known agent, resveratrol with the cocrystal. Resveratrol has been previously been tested in life-span extension models in *drosophila* and has been shown to have modest effects (See Mech. Ageing Dev., 2007, 128: 546-552 and Proc. Natl. Acad. Sci. USA, 2004, 101:12980-85). The percentage of surviving flies in untreated group or flies fed with either 100 mg/kg body weight/day of resveratrol or 100 mg/kg body weight/day of cocrystal was determined at the end of 9th day. While resveratrol showed a modest effect in the early time points, at day 9 it had no statistically different effect compared to untreated flies (FIG. 7). However the cocrystal had a dramatic effect and nearly doubled the number of surviving flies (FIG. 7). This study shows that in an in vivo model where the flies die due to neurodegeneration caused by human APP over expression, the cocrystal is able to provide robust protection against neurodegeneration and death.

It should be noted that, as used in this specification and the appended claims, the singular forms "a," "an," and "the" include plural references unless the content clearly dictates otherwise. Thus, for example, reference to a composition containing "a compound" may include a mixture of two or more compounds. It may also be noted that the term "or" is generally includes "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be noted that many variations and modifications may be made while remaining within the scope of the invention.

What is claimed is:

1. A pharmaceutical composition comprising a niacin hybrid resulting from esterification of niacin with apocynin and wherein the said composition is effective in treatment of a disorder or a disease characterized by excess production of amyloid beta peptide-42 (Abeta42), its deposition, accumulation, and plaque formation.

2. A method of treatment of a human disorder or a disease condition caused by excess production of amyloid beta peptide-42 (Abeta42), its deposition, accumulation, and plaque formation comprising administering a therapeutically effective amount of the pharmaceutical composition as claimed in claim 1.

3. The method of claim 2 wherein the said human disorder or disease condition is selected from the group consisting of Alzheimer's disease, dementia and mild cognitive impairment and other neurodegenerative disorders selected from Parkinson's disease and ischemic stroke.

4. The method of claim 2 wherein the said pharmaceutical composition is administered orally or parenterally.

5. A pharmaceutical composition comprising at least one pharmaceutically acceptable carrier, diluent or an excipient and a compound according to claim 1.

6. The method of claim 2 wherein the said pharmaceutical composition is administered in combination therapy with other existing small molecule, protein, vaccine or nucleic acid based approved drugs or those in development for treatment of Alzheimer's disease, dementia's or mild cognitive impairment or other neurodegenerative disorders selected from Parkinson's disease and ischemic stroke.

* * * * *